United States Patent
Srocka et al.

(10) Patent No.: US 9,500,582 B2
(45) Date of Patent: Nov. 22, 2016

(54) METHOD FOR DETECTING BURIED LAYERS

(71) Applicant: HSEB Dresden GmbH, Dresden (DE)

(72) Inventors: Bernd Srocka, Berlin (DE); Ralf Langhans, Dresden (DE)

(73) Assignee: HSEB Dresden GmbH, Dresden (DE)

( * ) Notice: Subject to any disclaimer, the term of this patent is extended or adjusted under 35 U.S.C. 154(b) by 0 days.

(21) Appl. No.: 14/500,631

(22) Filed: Sep. 29, 2014

(65) Prior Publication Data

US 2015/0014542 A1 Jan. 15, 2015

Related U.S. Application Data

(63) Continuation-in-part of application No. PCT/EP2013/055532, filed on Mar. 18, 2013.

(51) Int. Cl.

| | | |
|---|---|---|
| G01J 5/02 | (2006.01) | |
| G01N 21/55 | (2014.01) | |
| G01N 21/84 | (2006.01) | |
| G01N 21/95 | (2006.01) | |
| G01N 33/00 | (2006.01) | |

(52) U.S. Cl.
CPC .......... *G01N 21/55* (2013.01); *G01N 21/8422* (2013.01); *G01N 21/9505* (2013.01); *G01N 33/00* (2013.01); *G01N 2021/8438* (2013.01); *G01N 2033/0095* (2013.01); *G01N 2201/068* (2013.01)

(58) Field of Classification Search
CPC ... G01N 21/3581; G01N 21/00; G01N 21/35
See application file for complete search history.

(56) References Cited

U.S. PATENT DOCUMENTS

| | | | |
|---|---|---|---|
| 5,381,234 A * | 1/1995 | Barbee et al. | 356/369 |
| 5,424,536 A | 6/1995 | Moriya | |
| 6,734,960 B1 | 5/2004 | Goto et al. | |
| 8,179,530 B2 * | 5/2012 | Levy et al. | 356/401 |
| 2004/0223141 A1 | 11/2004 | Rosengaus | |
| 2004/0239920 A1 | 12/2004 | Kreh et al. | |
| 2008/0002753 A1* | 1/2008 | Timans | 374/2 |
| 2008/0212096 A1* | 9/2008 | Kumar | 356/369 |
| 2013/0162996 A1* | 6/2013 | Straaijer et al. | 356/369 |

FOREIGN PATENT DOCUMENTS

| | | |
|---|---|---|
| DE | 69017947 T2 | 3/1995 |
| DE | 69026926 T2 | 5/1996 |
| DE | 6913 245 T2 | 9/1998 |

(Continued)

*Primary Examiner* — David Porta
*Assistant Examiner* — Hugh H Maupin
(74) *Attorney, Agent, or Firm* — Thorpe North & Western LLP

(57) ABSTRACT

An arrangement for optically detecting buried layers of flat objects having a plurality of layers, in particular wafers, containing a radiation source for illuminating the surface of the object at an angle; a polarization filter arranged in the beam path; and a detector for detecting radiation reflected by the surface of the object or transmitted by the object; is characterized in that that layer of the object which is closest to the radiation source at least partially transmits the radiation from the radiation source; the polarization filter transmits only radiation which is polarized parallel to the plane of incidence; and the surface of the object is illuminated at the Brewster angle. The surface of the object is preferably illuminated with unpolarized radiation and the polarization filter is arranged in the beam path between the surface of the object and the detector.

12 Claims, 3 Drawing Sheets

(56) References Cited

FOREIGN PATENT DOCUMENTS

| DE | 10027780 | A1 | 1/2001 |
|---|---|---|---|
| DE | 102007043937 | B4 | 3/2008 |
| EP | 0397388 | B1 | 3/1995 |
| EP | 0439881 | B1 | 5/1996 |
| EP | 0469572 | B1 | 9/1998 |

* cited by examiner

METHOD FOR DETECTING BURIED LAYERS

TECHNICAL FIELD

The invention relates to an assembly for optical detection of buried layers of flat objects with a plurality of layers, in particular wafers, comprising:
(a) a radiation source for illuminating the surface of the object;
(b) a polarization filter arranged in the path of rays; and
(c) a detector for the detection of radiation reflected by the surface of the object or transmitted by the object.

In different industry branches, flat products and their properties are inspected with optical imaging methods. In the semiconductor and flat panel industry these flat products are, amongst others, wafers. Wafers are discs made of semiconductor-, glass-, sheet- or ceramic materials. In various processing steps during manufacturing, different materials are arranged on top of each other and thereby stacks with layers are produced.

Exact knowledge of the generated layers is required for production control and quality management. For different reasons, however, it is often not possible to carry out a full inspection of the work piece after inserting a new material layer. In other cases, certain layers or spaces are formed only after processing by inserting a cover layer. Therefore, they are not directly accessible. Special analysis methods should enable analysis to reach buried layers. For economic reasons it is desirable to generate the required information with a method which will not destroy the object. Furthermore, the results should be available within a short period of time in order to avoid disturbance of the production flow due to the inspection.

PRIOR ART

Presently, mainly ellipsometry measurements are used for destruction-free layer analysis.

The properties of the layers are determined with the change of the polarization state of polarized, incident radiation when reflected or transmitted at the borders between the layers. At first, polarized radiation is generated with a polarizer. A point on the object is illuminated with such polarized radiation. The change of the polarization state of the reflected or transmitted radiation is determined with an analyzer.

Ellipsometric measurements are highly sensitive but only work point-wise. Therefore, a series of discrete measuring points must be taken and interpolated in order to determine the layer properties over an area. The ellipsometric measuring procedure requires considerable measuring time for each inspected point, because usually mechanical parts, such as the analyzer, must be moved. Ellipsometric measurements are, therefore, not suitable for area inspections with high throughput requirements.

Furthermore, there are a series of methods for inspection of layers which do not operate without destruction. An example for such a method is scanning electron microscopy. The samples, however, must be cut perpendicular to the layers. Thereby, the sample cannot be used anymore.

DISCLOSURE OF THE INVENTION

It is an object of the invention to provide an assembly of the above mentioned kind which operates destruction-free and where a portion or the entire area of a layer below the surface of an object can be inspected with high speed.

According to an aspect of the invention this object is achieved in that
(d) the layers of the object which are nearest to the radiation source are at least partly transparent for the radiation of the radiation source;
(e) the polarization filter is transparent only for radiation which is polarized parallel to the plane of incidence; and
(f) the illumination of the surface of the object is effected under Brewster-angle.

With such an assembly it is possible to detect the presence or the absence of a layer in suitable stacks of layers. The measurements only require little efforts and operate with high throughput rates without destruction.

In particular, the surface of the object can be illuminated with non-polarized radiation and the polarization filter can be positioned in the path of rays between the surface of the object and the detector.

The transmission of the radiation can be achieved by suitable selection of the wavelength range used to illuminate the object. A particularly suitable wavelength range for wafers and semiconductor substrates is the infrared range between 1 micron and 9 microns.

The Brewster angle depends on the material. At the boundary layer between two materials with different refractive indices $n_1$ and $n_2$ the reflected portion is for radiation incident from the medium with the refractive index $n_1$ under Brewster angle relative to the axis of incidence polarized perpendicular to the plane of incidence. The following equation applies for Brewster angle:

$$\alpha = \arctan\left(\frac{n_2}{n_1}\right)$$

The remaining radiation, i.e. the entire parallel polarized portion of the radiation and a portion of the perpendicular polarized radiation is transferred into the medium with the refractive index $n_2$.

The reflected radiation passes a filter which lets only radiation pass which is polarized in parallel to the incident plane. No radiation would be detected behind the filter for the layer stack described above.

According to Snellius' law the radiation travels in the medium with the refractive index $n_2$ in a direction with the angle $$\alpha' = \arctan\left(\frac{n_1}{n_2}\sin\alpha\right)$$

relative to the axis of incidence. If a further layer in the stack is hit having again the refractive index $n_1$ the radiation is again incident on the boundary area under Brewster angle. It can easily be shown that the Brewster angle for the transition from $n_2$ to $n_1$ is exactly $\alpha'$. Consequently, perpendicular polarized radiation is reflected at this boundary area. Generally, only perpendicularly polarized radiation is reflected if the media of an entire layer stack including the incident medium have only two different refractive indices.

If at any position in the layer stack there is a third material having a different refractive index $n_3$, which is different to $n_1$ and $n_2$, the intermediate boundary area is not illuminated under Brewster angle relative to the layer above. In such a case parallel polarized portions of the radiation are now reflected also. The reflected radiation passes the layer stack in reverse order. It exits the surface and can pass the filter. The transmitted radiation is detected with a detector system.

The method can be used with the layer stack with the properties described above for a positive check as well as for a negative check. The positive check determines if a certain layer is fully present or at least in certain areas. For this purpose local decreases in the bright images are searched. The negative check determines if a certain layer is not present at all or only in certain areas. For this purpose only local increases of brightness in a mainly dark image are relevant.

Contrary to ellipsometry full scanning of an area of the sample is possible. The results are available quasi immediately. The assembly requires only little efforts and can be used with little costs. Furthermore, high throughput rates are possible.

According to the invention the detector can be positioned such that the reflected radiation is detected. In an alternative embodiment of the invention the assembly can be used in transmission mode. The reflection at a layer with the refractive index $n_3$ reduces the parallel polarized radiation observed in transmission mode and thereby enables the detection of the presence or absence of this layer. As this will cause only a reduction rather then the full deletion of the radiation used for the detector such modification is particularly suitable to investigate local differences.

A macroscopic detection system is provided in a further modification of the invention, comprising a macroscope illumination optics and a photographic objective. Alternatively or additionally a microscopic detection system can be provided comprising a microscope illumination optics and a microscope objective.

Depending on the application, macroscope or microscopic assemblies can be used as a detecting system. Preferred are in particular line-detector scanning assemblies where a line is oriented horizontally above the sample. With such embodiment of the invention perspective aberrations and dependencies of an optic-dependent, sometimes limited field depth is eliminated. The detector can be a photographic or electrooptical receiver, in particular a CCD, CMOS, or a focal plane array based on light-sensitive materials such as Si, Ge, or InGaAs in the form of a line- or array detector simultaneously detecting a plurality of image points.

Means can be provided for realizing a visual observation of the radiation reflected by the object or transmitted by the object and passing the polarization filter. Such means can be a screen or preferably an eyepiece.

Depending on the application it can be provided that an immersion solution having selected refractive index is provided on top of the uppermost layer of the object. In the above described modification of the invention the layer with the refractive index $n_1$ is air or an immersion solution having a refractive index corresponding to the one of the layers in the inspected layer stack. The refractive index is, therefore, either $n_1$ or $n_2$.

If it is mainly the task to inspect local differences in the presence or absence of a layer with the refractive index $n_3$ such limitation can be omitted. In this case a reflected radiation portion is obtained at the transition air/first layer in form of radiation which is polarized parallel to the plane of incidence. This radiation intensity, however, is modulated by occurring or missing reflection at the layer with $n_3$ whereby the layer with $n_3$ can be tested. Preferably, a broad hand radiation source would be used for this embodiment in order to reduce the influence of layer-thickness caused interferences.

Further modifications of the present invention are subject matter of the subclaims. An embodiment is described below in greater detail with reference to the accompanying drawings.

DESCRIPTION OF THE EMBODIMENT

Figure 1:
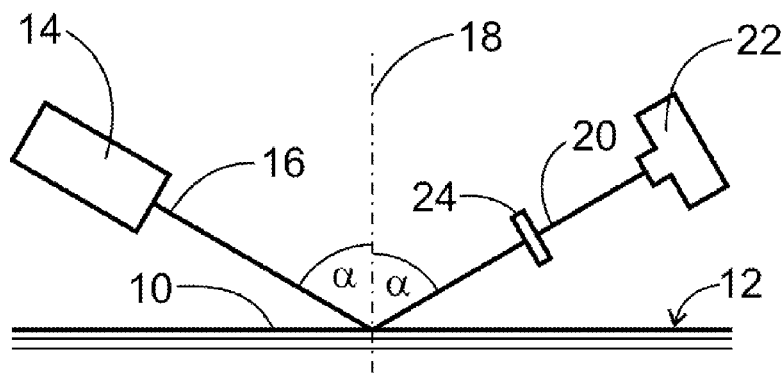
FIG. 1 is a schematic view of a measuring assembly for the inspection of objects with several layers.
Figure 3:
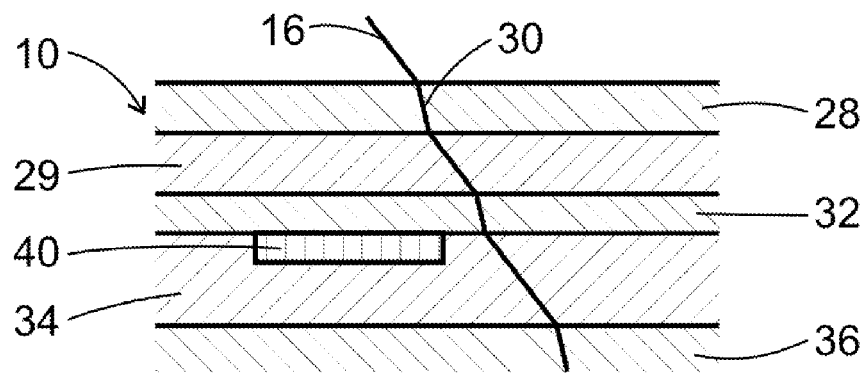
FIG. 3 shows a section of an object with several layers having alternating refractive indices.
Figure 4:
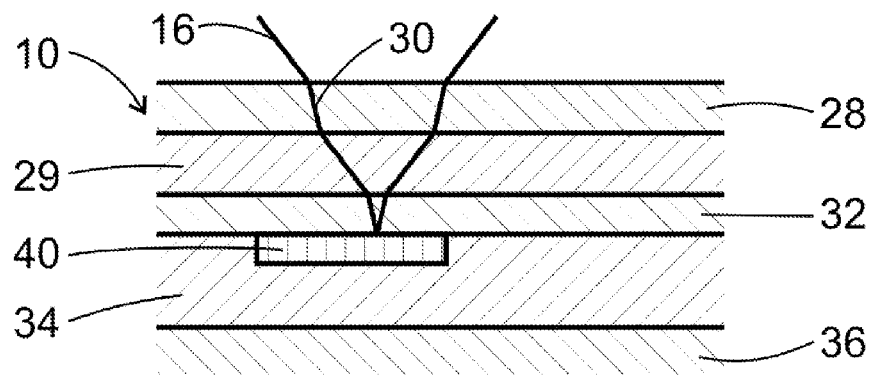
FIG. 4 shows the object of FIG. 3 with a radiation path in the range of a defect.

FIG. 1 shows an object generally designated with numeral 10. In the present embodiment the object 10 is a wafer with a silicon substrate 28, 32, and 36 having several vertically stacked, air-filled spaces 29 and 34. The spaces 29 and 34 are separated from each other by small layers 32 and 36 of silicon as can be seen in FIGS. 3 and 4. Due to production conditions in some of the spaces 29 and 34 defects can occur in the form of silicon oxide layers 40. This corresponds to the negative check.

Each of the materials, i.e. silicon, silicon oxide and air are defined by their refractive index $n_x$. The refractive index of the uppermost layer 28 of silicon is 3.5. The refractive index of the air layer 29 therebelow is 1.0. FIG. 1 schematically illustrates the measuring assembly. The surface 12 of the object is illuminated with infrared radiation 16 from an infrared radiation source 14. In the present embodiment broad band radiation from the wavelength range between 1.1 microns and 1.6 microns is used.

The parallel radiation bundle illuminates an area of about 5×5 m². The illumination is effected with an angle of $\alpha = \arctan n_2/n_1 = \arctan 3.1/1.0 = 74°$ with respect to the surface normal 18. This is the Brewster angle for the transition from air to silicon. A measurement in the angular range about ±3 about the Brewster angle between the incident medium and the surface 12 will also provide acceptable results. A portion of the radiation bundle 16 is reflected. The reflected radiation 20 is detected with a CCD area detector 22 and is available for further processing. A polarizer 24 is arranged in the path of rays between the surface 12 of the wafer and the detector. The polarizer is directed in such a way that only radiation is transmitted which has a polarization direction parallel to the illumination plane.

Figure 2:
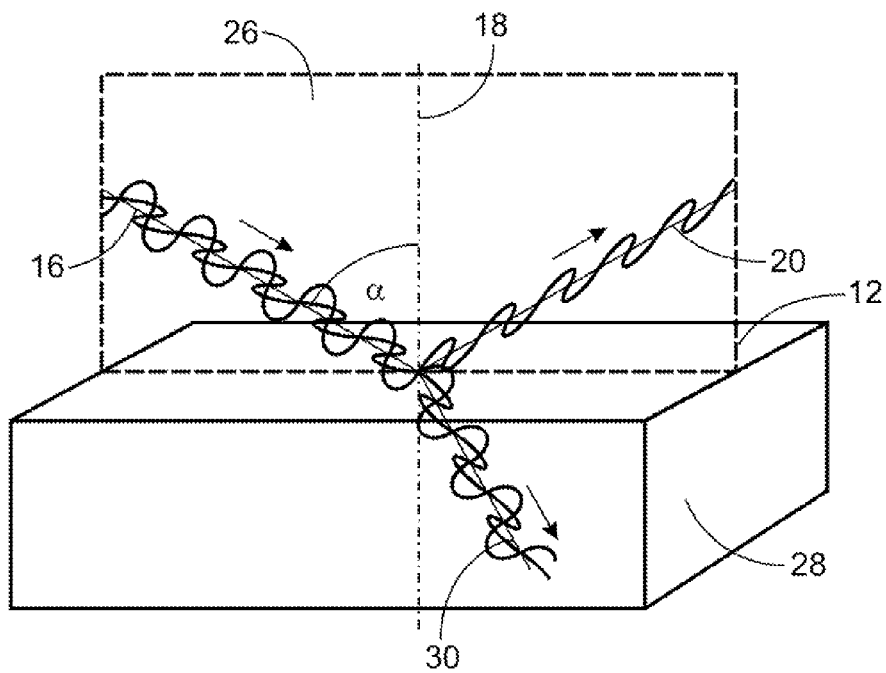
FIG. 2 illustrates the reflection and transmission when the object is illuminated under Brewster angle with an assembly shown in FIG. 1.

This is illustrated in FIG. 2. The illumination plane is designated with numeral 26. It runs through the surface normal 18 and comprises the incident radiation 16 as well as the reflected radiation 20. The radiation 16 is non-polarized, i.e. the distribution of the polarization directions are randomly distributed in all directions. As the radiation is incident on the object under Brewster angle only radiation is reflected at first which has a polarization direction perpendicular to the illumination plane 26. This radiation is blocked by the polarizer 24.

The wavelength of the radiation is selected such that the object is transparent for the radiation in the present embodiment. The remaining radiation 30 will, therefore, enter the uppermost layer 28 of the object.

FIGS. 3 and 4 show the layer structure of the object 10. The layers 29 and 34 are air-filled spaces and have, therefore, the same refractive index as the medium from where the radiation falls on the object. The uppermost layer 28, the intermediate layer 32 and the substrate 36 consist of silicon. The layer 40 consists of silicon oxide having a refractive index which is neither the refractive index of air nor of silicon. Such a layer occurs in the object 10 only at certain positions and therefore represents a defect which should be detected.

The path of rays shown in FIG. 3 shows the parallel polarized portion. It can be recognized that the radiation is incident at the transitions between the layers 29 and 32 and between the layers 34 and 36 under the same angle on the surface, which is the Brewster angle. Due to the above described relation the illumination at the transitions between the layers 28 and 29 as well as 32 and 34 is effected under Brewster angle. At such transitions only radiation is reflected which has a polarization direction perpendicular to the illumination plane 26. Such radiation is blocked by the polarizer 24. The remaining radiation, in particular, the parallel polarized portion is transmitted to the respective next layer. As long as the disturbing layer 40 is not met, as shown in FIG. 3, the object 10 will not reflect any parallel polarized radiation. No signal is registered by the detector 22.

FIG. 4 shows the layer structure of FIG. 3 for radiation incident on the disturbing layer 40. The transition between the layers 32 and 40 is not illuminated under Brewster angle due to the deviating refractive index of layer 40. Consequently, a portion of the radiation with polarizing direction parallel to the illumination plane is reflected. Such radiation will pass the layers in the opposite direction, can pass the polarizer and be detected.

Figure 5:
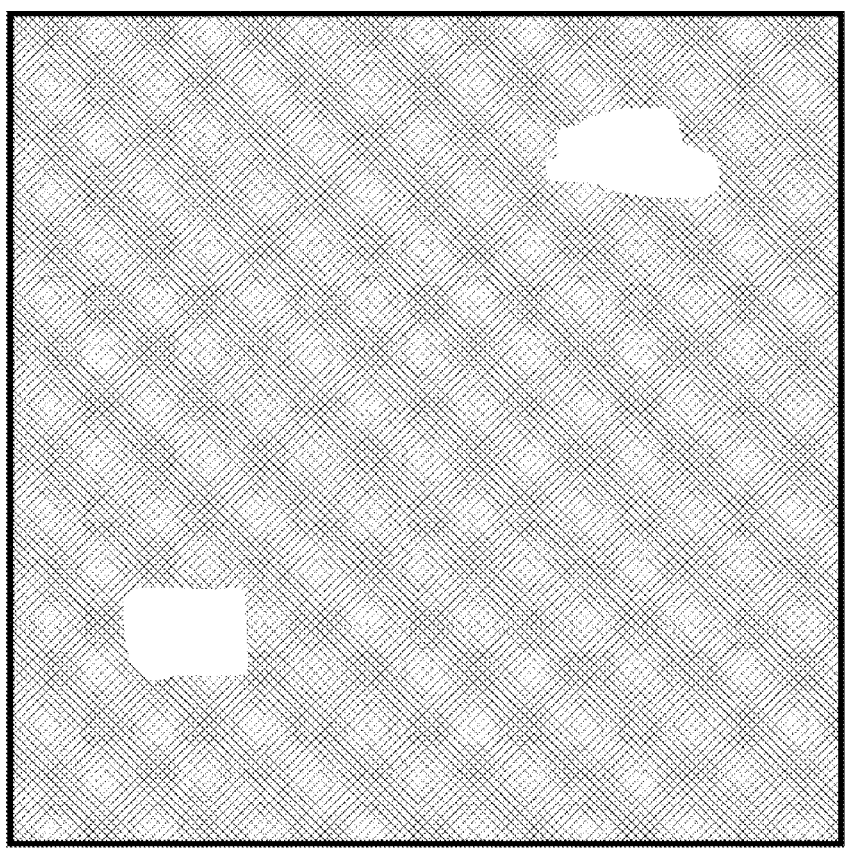
FIG. 5 is a schematic representation of an image of the object of FIGS. 3 and 4 taken with a detector.

A typical image taken with the detector 22 is schematically shown in FIG. 5. The bright ranges are locations where the silicon oxide layer 40 is present. The other regions of the image appear dark.

As long as the wafer is constituted only by a repeating layer structure no signal will be detected by the detector. Defects by materials with a different refractive index will cause that the incident angle at the transition to this layer is not Brewster angle anymore. On the other hand it may be desired that there is a layer with a different refractive index present, i.e. that a signal is always detected by the detector 22. Then its absence will be detected.

The invention was described above in relation to a precise embodiment in order to facilitate its understanding. It is understood, however, that the invention can be put into practice in many other ways also. Different materials with different refractive indices and light with different wavelengths can be used without having an influence on the scope of the invention, which is exclusively determined by the appended claims.

What is claimed is:

1. A method for optical detection of the presence or the absence of buried layers in wafers or other flat objects having a plurality of layers and a surface, comprising:
 (a) illuminating a portion or the entire area of said surface of said object using a radiation source emitting radiation as a path of rays and thereby defining a plane of incidence,
 (b) detecting if radiation is reflected by said object or transmitted by said object, detection of radiation reflected by said object or reduction of radiation transmitted by said object indicating the presence of a buried layer;
 (c) arranging a polarization filter in said path of rays between the radiation source and the detector whereby the radiation detected by the detector is polarized;
 wherein
 (d) said layers of said object which are nearest to said radiation source are at least partly transparent to said radiation generated by said radiation source;
 (e) said polarization filter is transparent only for radiation which is polarized parallel to said plane of incidence;
 (f) said illumination of said surface of said object is effected under Brewster-angle, and
 (g) apart from the buried layer to be detected, each layer, including the layer of incidence, has one of two different refractive indices.

2. The method of claim 1 and wherein the step of illuminating said surface of said object illuminates said surface with non-polarized radiation, and wherein the step of arranging a polarization filter in said path of rays is arranging said polarization filter in said path of rays between said surface of said object and said detector.

3. The method of claim 1 and wherein the step of illuminating said surface of said object illuminates said surface with radiation in the infrared wavelength range.

4. The method of claim 1 and wherein the step of detecting radiation reflected by said surface of said object or transmitted by said object is the step of providing a macroscopic detection system comprising a macroscope illumination optics and a photographic objective to detect said radiation.

5. The method of claim 1 and wherein the step of detecting radiation reflected by said surface of said object or transmitted by said object is the step of providing a microscopic detection system comprising a microscope illumination optics and a microscope objective to detect said radiation.

6. The method of claim 1 and wherein the step of detecting radiation reflected by said surface of said object or transmitted by said object is the step of providing a photographic or electrooptical receiver, in particular a CCD, CMOS, or a focal plane array based on light-sensitive materials such as Si, Ge, or InGaAs in the form of a line- or array detector simultaneously detecting a plurality of image points to detect said radiation.

7. The method of claim 1 and additionally providing means for realizing a visual observation of said radiation reflected by said object or transmitted by said object and passing said polarization filter.

8. The method of claim 1 wherein said stack of layers has an uppermost layer which is closest to said radiation source and additionally immersing the top of said uppermost layer of said object in an immersion solution having a selected refractive index.

9. The method of claim 1 wherein all layers of said object are transparent for said radiation from said radiation source.

10. The method of claim 1 and wherein the step of detecting radiation reflected by said object or transmitted by said object is the step of simultaneous detecting with a line or array detector said radiation reflected by a plurality of image points of said object or transmitted by a plurality of image points of said object thereby obtaining a full scanning of said area of said object.

11. A method for optical detection of the presence or the absence of buried layers in wafers or other flat objects having a plurality of layers and a surface, comprising:
  (a) illuminating a portion or the entire area of said surface of said object using a radiation source emitting radiation as a path of rays and thereby defining a plane of incidence,
  (b) detecting if radiation is reflected by said object, detection of radiation reflected by said object indicating the presence of a buried layer;
  (c) arranging a polarization filter in said path of rays between the radiation source and the detector whereby the radiation detected by the detector is polarized;
  wherein
  (d) said layers of said object which are nearest to said radiation source are at least partly transparent to said radiation generated by said radiation source;
  (e) said polarization filter is transparent only for radiation which is polarized parallel to said plane of incidence;
  (f) said illumination of said surface of said object is effected under Brewster-angle, and
  (g) apart from the buried layer to be detected, each layer, including the layer of incidence, has one of two different refractive indices.

12. The method of claim 11 and wherein the step of detecting radiation reflected by said object is the step of simultaneous detecting with a line or array detector said radiation reflected by a plurality of image points of said object thereby obtaining a full scanning of said area of said object.

* * * * *